(12) United States Patent
Berkane et al.

(10) Patent No.: US 9,684,770 B2
(45) Date of Patent: Jun. 20, 2017

(54) PERFORMING MEASUREMENT OF A SUBJECT

(75) Inventors: Rafih Berkane, Eindhoven (NL);
Marijn Christian Damstra, Eindhoven (NL); Robert Paul Koster, Eindhoven (NL); Stefan Katzenbeisser, Darmstadt (DE); Milan Petkovic, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 340 days.

(21) Appl. No.: 13/125,115

(22) PCT Filed: Oct. 16, 2009

(86) PCT No.: PCT/IB2009/054556
§ 371 (c)(1),
(2), (4) Date: Oct. 31, 2011

(87) PCT Pub. No.: WO2010/046820
PCT Pub. Date: Apr. 29, 2010

(65) Prior Publication Data
US 2012/0108910 A1    May 3, 2012

(30) Foreign Application Priority Data

Oct. 22, 2008   (EP) ..................................... 08167279

(51) Int. Cl.
*A61B 5/00*    (2006.01)
*G06Q 10/00*   (2012.01)
(Continued)

(52) U.S. Cl.
CPC ............ *G06F 19/36* (2013.01); *A61B 5/0002* (2013.01); *G06F 19/3412* (2013.01);
(Continued)

(58) Field of Classification Search
CPC .. G06F 19/36; G06F 19/3412; G06F 19/3418; G06F 19/322; A61B 5/0002; A61B 2560/0271; G01N 35/00613
See application file for complete search history.

(56) References Cited

U.S. PATENT DOCUMENTS 5,448,991 A * 9/1995 Polson et al. ................. 600/330
5,503,148 A * 4/1996 Pologe et al. ................ 600/323
(Continued)

FOREIGN PATENT DOCUMENTS

WO    2007062558        5/2007
WO    2007100959 A2    9/2007

OTHER PUBLICATIONS

Van Deursen, T. et al. "Hedaquin: A Reputation-based Health Data Quality Indicator", Electronic Notes in Theoretical Computer Science 197 (2008) 159-167.

*Primary Examiner* — William Thomson
*Assistant Examiner* — Shirley Jian

(57) ABSTRACT

A method of performing measurement of a subject comprises measuring a physiological parameter of a subject, deriving data from the measured parameter, optionally, obtaining metadata relating to the measurement of the physiological parameter, determining the quality of the derived data from the derived data and/or the obtained metadata, and if the determined quality matches a predefined criteria, performing a predefined corrective action. In one embodiment, the method further comprises calculating one or more qualifiers from the derived data and/or from the obtained metadata, and wherein the step of determining the quality of the derived data comprises determining the quality of the derived data from the calculated qualifiers.

14 Claims, 6 Drawing Sheets

(51) Int. Cl.
  *G06F 19/00*    (2011.01)
  *G01N 35/00*    (2006.01)

(52) U.S. Cl.
  CPC ........ *G06F 19/3418* (2013.01); *A61B 5/7267* (2013.01); *A61B 2560/0271* (2013.01); *G01N 35/00613* (2013.01); *G06F 19/322* (2013.01)

(56) References Cited

U.S. PATENT DOCUMENTS

| | | | | |
|---|---|---|---|---|
| 5,934,277 | A * | 8/1999 | Mortz | 600/323 |
| 6,035,223 | A * | 3/2000 | Baker, Jr. | 600/323 |
| 6,345,195 | B1 * | 2/2002 | Herskowits et al. | 600/473 |
| 6,449,501 | B1 * | 9/2002 | Reuss | 600/323 |
| 6,654,624 | B2 * | 11/2003 | Diab et al. | 600/336 |
| 7,006,856 | B2 * | 2/2006 | Baker, Jr. | A61B 5/024 600/300 |
| 7,471,969 | B2 * | 12/2008 | Diab et al. | 600/323 |
| 7,998,069 | B2 * | 8/2011 | Zivitz et al. | 600/300 |
| 8,095,192 | B2 * | 1/2012 | Baker et al. | 600/310 |
| 8,184,866 | B2 * | 5/2012 | Takaku et al. | 382/115 |
| 2004/0138540 | A1 | 7/2004 | Baker, Jr. et al. | |
| 2005/0215868 | A1 | 9/2005 | Kenjou et al. | |
| 2006/0089542 | A1 | 4/2006 | Sands | |
| 2007/0197881 | A1 | 8/2007 | Wolf et al. | |
| 2008/0009680 | A1 | 1/2008 | Hassler | |
| 2008/0162182 | A1 | 7/2008 | Cazares et al. | |
| 2012/0108910 | A1 | 5/2012 | Berkane et al. | |
| 2013/0259012 | A1 * | 10/2013 | Gormley et al. | 370/336 |

* cited by examiner

1

| i | j | |
|---|---|---|
| | | 1 |
| 0 | | — |
| 1 | | 66,20 |
| 2 | | 66,50 |
| 3 | | 66,80 |
| 4 | | 66,40 |
| 5 | | 67,00 |
| 6 | | 66,80 |
| 7 | | 77,20 |
| 8 | | 66,90 |
| 9 | | 66,50 |

2

| | |
|---|---|
| $\mu_{(1,9,1)}$ | 67,81 |
| $\sigma_{(1,9,1)}$ | 3,33 |
| B | 2,00 |
| $B\sigma_{(1,9,1)}$ | 6,66 |

3

| $\|a_{(i,j)} - \mu_{(f,g,j)}\|$ |
|---|
| 1,61 |
| 1,31 |
| 1,01 |
| 1,41 |
| 0,81 |
| 1,01 |
| 9,39 |
| 0,91 |
| 1,31 |

4

| $\|a_{(i,j)} - \mu_{(f,g,j)}\| \leq B\sigma_{(f,g,j)}$ |
|---|
| TRUE |
| TRUE |
| TRUE |
| TRUE |
| TRUE |
| TRUE |
| FALSE |
| TRUE |
| TRUE |

5

| st(i,j) |
|---|
| 0,76 |
| 0,80 |
| 0,85 |
| 0,79 |
| 0,88 |
| 0,85 |
| 0,00 |
| 0,86 |
| 0,80 |

PERFORMING MEASUREMENT OF A SUBJECT

FIELD OF THE INVENTION

This invention relates to a method of, and system for, performing measurement of a subject. In one embodiment, the invention improves measurement quality in tele-health applications using quality indications and feedback signals.

BACKGROUND OF THE INVENTION

It is common now for patients to use personal health devices, for example to measure their weight or calculate their blood pressure. The results of the measurements can be used for different purposes. The measurement data is in the first place intended to provide the patient with health information. This information can also be exchanged with the patient's health service provider. If this is done remotely, the health provider can give feedback remotely, which saves time for both parties. This can offer an efficient and effective way of providing health care. The remote delivery of healthcare services can be regarded as the field of "tele-health".

Within the domain of tele-health, measurement devices play an important role since they should provide objective information on physical (or physiological) conditions of the human body. This measurement data serves in the first place an informative purpose, for the person taking the measurements. The health data can however also be relevant for health care providers to make a diagnosis of a patient's health status. An increasing number of services, such as remote patient management, and elderly and fitness services make use of a tele-health architecture in which the measurement devices are connected to remote backend servers. Health care providers use this architecture to remotely access the measurement data and help the patients. Continua (see http://www.continuaalliance.org/) is a standardization body for personal tele-health and well being. It standardizes protocols between measurement devices, gateway (application hosting) devices and online healthcare/wellness services.

There exists the problem that healthcare measurement data obtained from patient measurement devices is not always of satisfactory quality and that remote (IT systems of) healthcare professionals have no practical and effective means to influence the quality. Related to the above problem is the question how in remote patient monitoring and tele-health applications the health care provider can help the patient and make a diagnosis without having any knowledge of quality/reliability of the measurement taken (for example, the circumstances and the conditions in which the measurement is taken).

Currently, the health care provider cannot estimate objectively how well the measurement has been performed, not even on the basis of the patient's information or experience. Typically, the person performing the measurement has received limited or no instruction on how to use the measurement device. However, healthcare providers require guaranteed sufficient quality of the measurement data, which is only the case if the measurement is taken under predefined circumstances and conditions which makes the data more reliable for diagnosis. The Continua alliance does not prescribe the quality of the data. However, it could provide the means to be able to transfer the quality and context of the data. This can be done by supporting quality and context metadata in its data models and protocols. Recent research on health data quality indication (see Ton van Deursen, Paul Koster, Milan Petkovi•, Hedaquin, "A reputation-based health data quality indicator", 3rd International Workshop on Security and Trust Management, ESORICS 2007, Dreseden, Germany, 2007) proposes a system design which indicates the quality of health information based on ratings and reputation.

SUMMARY OF THE INVENTION

It is therefore an object of the invention to improve upon the known art.

According to a first aspect of the present invention, there is provided a method of performing measurement of a subject comprising measuring a physiological parameter of a subject, deriving data from the measured parameter, optionally, obtaining metadata relating to the measurement of the physiological parameter, determining the quality of the derived data from the derived data and/or from the obtained metadata, and if the determined quality matches a predefined criteria, performing a predefined corrective action.

According to a second aspect of the present invention, there is provided system for performing measurement of a subject comprising a sensor arranged to measure a physiological parameter of a subject, and to derive data from the measured parameter, optionally, a device arranged to obtain metadata relating to the measurement of the physiological parameter and a processor arranged to determine the quality of the derived data from the derived data and/or the obtained metadata, and, if the determined quality matches a predefined criteria, to perform a predefined corrective action.

Owing to the invention, it is possible for a healthcare provider system to take corrective action (for example by providing a feedback signal to a patient measurement device) to increase the measurement data quality to satisfactory levels, where the corrective action (device reconfiguration, instruction message, etc.) is determined based on a quality indication associated with earlier measurements, and where the quality is determined based on the measurement data and optionally metadata from the patient measurement device.

The accuracy of the quality determination can be improved by using metadata about the measurement taken from the patient. That metadata could be a wide variety of different data, such as the number of measurements taken, the current time, the subject's recent activity, position of the cuff of a blood pressure meter, data obtained from environmental sensors, etc. All of these things can be used to assist in the quality determination.

This system provides a method to improve the quality of measurements in such tele-health systems, such as those defined by the Continua Health Alliance. In one embodiment, metadata is associated with the measurement data. Subsequently, the measurement data quality is determined using the data (and if it exists, the metadata). Depending on the quality of the measured data, the health care provider (or any other party) decides whether to act upon the received data, for example, by performing (an update) of a patient's diagnosis and/or treatment. In one embodiment, the quality indication is used to create a feedback signal to the patient or their device, to improve the quality of the performed measurements. This feedback signal can be used to reconfigure the functionality of the measurement device, for example by changing the measurement process in a way to help the patient to overcome reoccurring mistakes or by making additional functionality available to those patients that consistently perform measurements with sufficient quality. Alternatively, the feedback signal informs the patient about the quality of their measurements together with (a reference to) additional instructions or training on how to operate the measurement device.

Advantageously, the method further comprises calculating one or more qualifiers from the derived data and/or the obtained metadata, and wherein the step of determining the quality of the derived data comprises determining the quality of the derived data from the calculated qualifiers. The measurement data (and/or the metadata) can be used to calculate statistical qualifiers, and the decision about the quality of the derived data can be made based upon these qualifiers. This provides a simple and effective method of handling the received data and metadata.

Preferably, the physiological parameter of the subject is measured by a first device, and the metadata relating to the measurement of the physiological parameter is obtained by a second device. In this embodiment, the accuracy of the quality determination is increased, as independent information is provided by the second device, such as an activity monitor, which can be used to provide additional information about the current status of the user.

The predefined corrective action could take many different forms. For example, in a first embodiment, the step of performing a predefined corrective action comprises providing feedback to the subject. This could be a message displayed to the subject via the measurement device that they are using, for example to instruct the user to make some adjustment in their measurement methodology. The feedback could also be provided by a different device, for example an email could be sent to the user, with further information in it, about the changes that the user should make.

In a second embodiment, the step of performing a predefined corrective action comprises (additionally or alternatively) performing a further measurement of the physiological parameter of the subject. If the quality of the subject's measurement data is perceived to be too low to be useful, then the measurement of the physiological parameter could be repeated, in order to attempt to obtain data that can be useful to a remote health professional. This can occur in real-time, so the user could take a measurement with a device, and the determination of the quality could be made straight away, and if the quality is too low, then the test can be repeated immediately.

In a further embodiment, the step of performing a predefined corrective action comprises (again additionally or alternatively) storing a component at a first device measuring the physiological parameter of the subject, the component adapting the future measurement of the physiological parameter of the subject. In this case, an amendment to the user's measurement scheme is made, but is only applied to future testing. For example, a blood pressure reading could be made based upon an average of three separate tests, and this might yield results that are too low in quality. In this case, the component could specify that future tests be based upon the average of five separate readings, as an amendment to the future measurement of the physiological parameter of the subject.

The predefined corrective action can comprise taking a decision in which the quality information can be used in that process. For example, it is possible to extend the system to include a decision making/support system that will take the quality data as input in the process of decision making. Then, during this process, for example, data with low quality will be used with lower weight then the data with high quality.

BRIEF DESCRIPTION OF THE DRAWINGS

Embodiments of the present invention will now be described, by way of example only, with reference to the accompanying drawings, in which:—

FIGS. 5 to 7 are tables used in the calculation of a stability qualifier, and

DETAILED DESCRIPTION OF THE EMBODIMENTS

Figure 1:
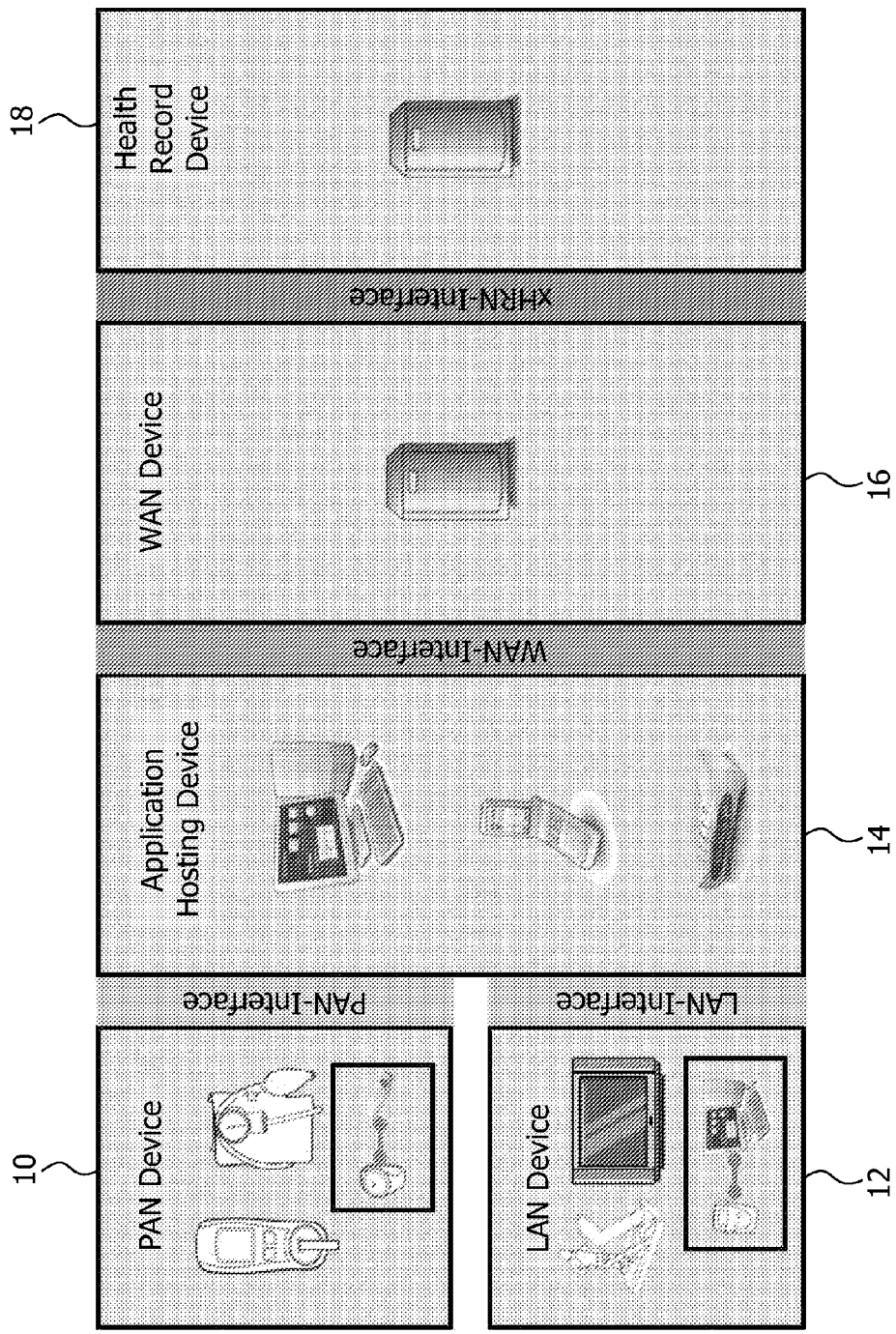
FIG. 1 is a schematic diagram of a healthcare system.

An example of a healthcare system, which provides tele-health to a subject, is shown in FIG. 1. Various PAN (personal area network) devices 10 are shown such as a wristwatch and a blood pressure measuring device, which includes a sensor for directly measuring physiological parameters of the subject. Additionally, LAN (local area network) devices 12 are provided such as a treadmill, which can also be used to gather healthcare information about the subject. The PAN devices 10 and the LAN devices 12 are connected via suitable interfaces (wired and/or wireless) to an appropriate application hosting device 14, such a computer or mobile phone, which will be local to the PAN and LAN devices 10 and 12.

The hosting device 14 will have installed a suitable application that is used in the system. The device 14 will run the application, which can gather and organise the outputs from the various PAN and LAN devices 10 and 12. The application hosting device 14 is connected to a WAN (wide area network) device 16 such as a server of a remote patient monitoring service or a wellness service. The WAN connection can be via a network such as the Internet. The connection to the WAN device 16 allows the subject to connect to various health services that are remote from their present location, which improves the delivery of health care services to the subject, and supports a faster and more efficient response time to the physiological condition of the subject.

The server 16 is also connected, via a suitable interface, to a health record device 18, which is maintaining a health record for the users of the system. Medical practitioners will have access to the health data stored on the record device 18. It is important that the data recorded by the individual health records stored by the device 18 is assigned, firstly to the correct user, and additionally, that the device which recorded the data is known with absolute certainty. It is also advisable that the relevant PAN or LAN device 10 or 12 is also approved for use in the system. In addition, it is important that the quality of the data acquired from the PAN and LAN devices 10 and 12 be monitored and controlled.

Figure 2:
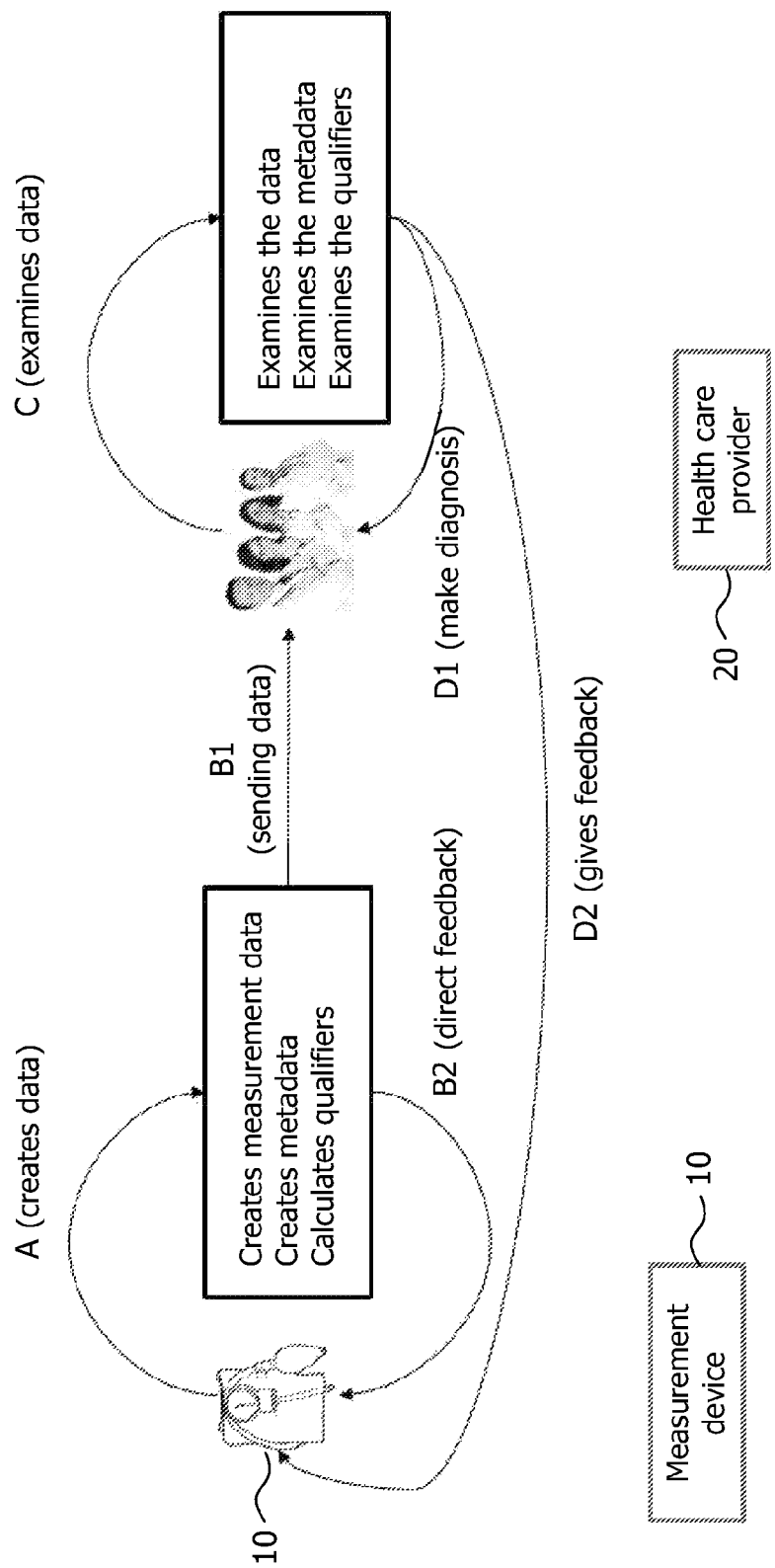
FIG. 2 is a further schematic diagram of the healthcare system.

In the system of the invention, the quality of measurements performed at remote locations in tele-health systems (such as Continua) is determined and associated with the measurement data, as illustrated in FIG. 2. FIG. 2 shows the architecture of tele-health system, including a feedback path to the patient.

A PAN device 10 (in this example, a blood pressure meter) creates measurement data (A). Additionally, and optionally, the device creates metadata. Metadata consists of information about the conditions and circumstances in which the measurement is taken. Based on the data (and optionally the metadata) it is possible for different qualifiers to be calculated, for example by the measurement device 10, the gateway (application hosting) device 14 or the backend system 18. Which system component calculates a qualifier may depend on the type of qualifier and on the system architecture, for example, which information is available at each system component. Qualifiers handle different data quality aspects.

The data, (and optionally metadata) and (if calculated) qualifiers are sent to the health care provider 20 (B1) or the device 10 gives direct feedback on this information (B2). Consequence of such direct feedback signal may be that the patient knows to what extent the measurement was performed successfully. Once the health care provider 20 receives the data it examines the data (C). On the basis of the data (and possibly metadata) and (if calculated) the qualifiers it decides to what extent the measurement procedure and/or data is of sufficient quality. If it is of sufficient quality the health care provider 20 can make a diagnosis (D1). If it is not, the (system of the) health care provider 20 can perform a corrective action, such as giving feedback to the patient (via the measurement device 10 for example) for taking the measurement again (D2). The latter may include reconfiguring the settings and functionality of the measurement device. The system of the health care provider 20 may also give a feedback signal in case of sufficient quality, for example to relax the measurement procedure, give a positive feedback message, or unlock more complex functionality.

Figure 3:
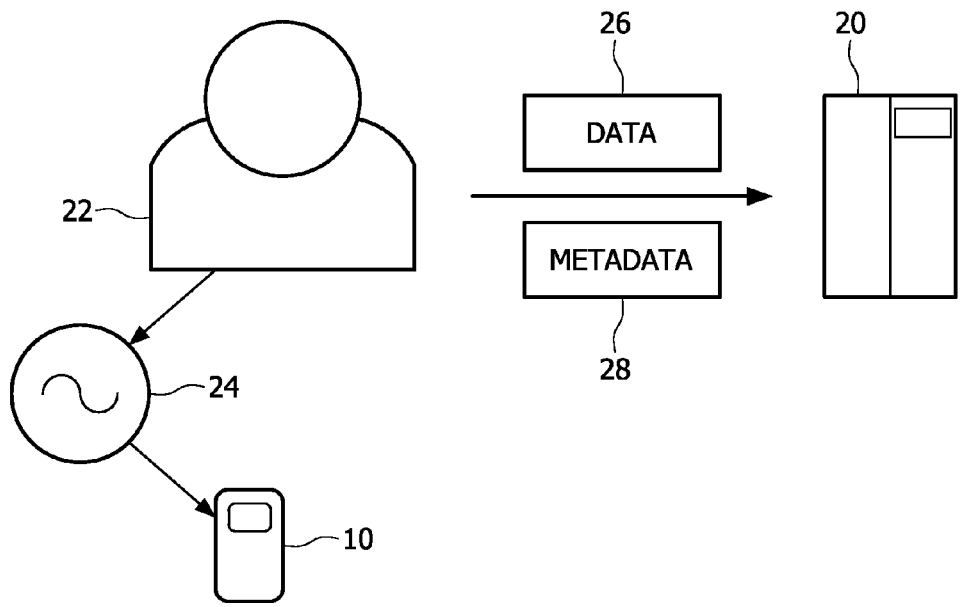
FIG. 3 is a schematic diagram showing data flow in the system.

FIG. 3 illustrates some of the data flow in the system, from the user side of the system, in the preferred embodiment of the invention. The subject 22 has a physiological parameter 24, such as their blood pressure, measured by a sensor of the device 10. The subject 22 is making this measurement themselves, without any direct outside influence or assistance. Data 26, which is derived from the measured parameter 24, and which may be the raw data acquired by the device 10, or may be calculations based upon that data, is sent, along with metadata 28 to the health care system 20. The metadata 28 may have been collected by the device 10, or may have been obtained by a different device, which is also connected into the local network, at the user's location.

Figure 4:
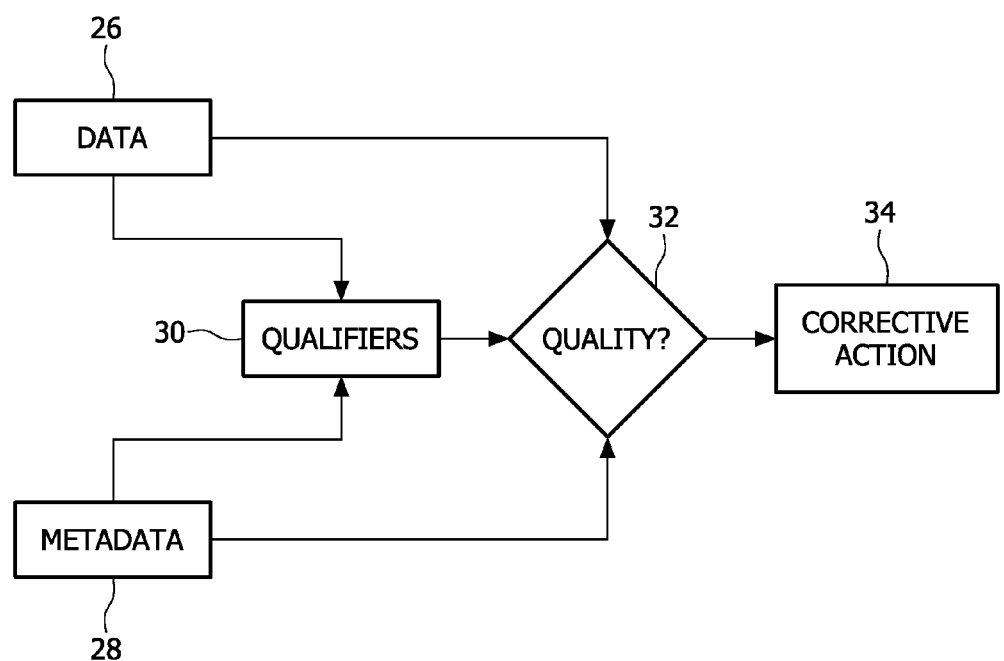
FIG. 4 is a schematic diagram showing further data flow in the system.

The remote health care system 20 receives the data 26, and metadata 28, sent by the subject 22, as can be seen in FIG. 4. From the data 26 and the metadata 28, qualifiers 30 can be calculated. A suitable processor at the system 20 will operate on the received data. These qualifiers 30 will allow a determination to be made as to whether the data 26 acquired by the device 10, from the subject 22, is of sufficient quality to be of use by the health care system 20 (or by implication, the health care professionals who access the data 26). In this embodiment, the qualifiers 30 are calculated at the server 20, not the device 10, but either implementation will provide a workable system.

Once the qualifiers 30 have been calculated, then there is a test stage 32, at which a test is made in relation to the qualifiers 30 to see if the data 26 is of sufficient quality. At this stage, there is determined the quality of the derived data 26 from the calculated qualifiers 30, and, if the determined quality matches a predefined criteria, such as being below a predefined threshold, there is performed a predefined corrective action 34. The nature of the corrective action 34 taken will depend upon a wide range of factors. For example, the original parameter 24 being measured, the input from the metadata 28 and the level of the quality can all be taken into account when making a decision on the corrective action to be taken.

The quality check 32 that is made to see if the quality matches the predetermined criteria, can be carried out in a number of ways. The use of the qualifiers 30 (which can be derived from either or both of the derived data 26 and the metadata 28) is the preferred embodiment, but it is not necessary to actually calculate any qualifiers 30. In the simplest version, the quality check 32 is carried out directly on either or both of the derived data 26 and the metadata 28. For example, the metadata 28 alone could be used to determine the quality of the derived data 26. Alternatively, the data 26 alone could be used to make a quality determination.

In FIG. 4, the corrective action 34 could be a feedback action, which is communicated back to the device 10 that the subject 22 used to take the original measurement. That feedback could also take many different forms. It could be something as a simple as a message to be output to the subject 22, such as an instruction to adapt the measurement process that the subject 22 is using or could be a feedback to instruct the user 22 to retake the test, for example. The feedback can be provided instantaneously, so that the user can readily associate the feedback with the measurement that they have just taken.

The quality estimation process, in the preferred embodiment, uses the qualifiers 30 as a basis for making a determination of whether the quality of the original test made by the subject 22 has yielded sufficient usable data 26 for accurate assessment of the subject's health needs. An example of a qualifier is the stability of certain series of measurements over time.

A first version of a stability formula is presented below, divided in two parts.

$$st(i, j) = \begin{cases} 1 - \frac{|a_{(i,j)} - \mu_{(f,g,j)}|}{B\sigma_{(f,g,j)}} & \text{if } |a_{(i,j)} - \mu_{(f,g,j)}| \leq B\sigma_{(f,g,j)} \\ 0 & \text{if } |a_{(i,j)} - \mu_{(f,g,j)}| > B\sigma_{(f,g,j)} \end{cases}$$

$$St_1(f, g, j) = \frac{\sum_{i=f}^{g} st(i, j)}{g - f + 1}$$

The working of the formula is explained in more detail below, with respect to sample data. In summary the formula works as follows. There is calculated, per measurement, the stability. At the end, $St_1(f, g, j)$ calculates the stability average of all measurements. The stability of one single measurement, calculated by $st_1(i, j)$, makes use of the standard deviation. It first calculates the difference between the measurement and the average of the whole series of the measurements of a certain property j. The difference is divided by B times the standard deviation. The latter is defined as the threshold. The stability is 0 in case if the difference exceeds the threshold.

FIG. 5 shows an example of the calculation of the stability qualifier, where there is measured the stability of the first property j=1. The data presented in step 1 represents a matrix $M_{(9,1)}$. The property weight in $a_{(0,1)}$ is not used so it can be left blank. The weight of the property parameter $a(0,x)$ is used to assign different weights to different properties when calculating some qualifiers (however, it is not applicable to the stability qualifier). For example, it could be used in the calculation of a completeness qualifier. It makes a difference if the measurement data itself is missing or the time of the measurement. Therefore different weights are assigned to these different properties and used in the calculation of a completeness qualifier. The weights can also be used to exclude certain properties from the calculation (if they are zero). These properties are then not taken into account while calculating the qualifier.

The second step, number 2, is the step of calculating statistical data on the basis of $M_{(9,1)}$. The calculated data, in order, are the measurement average, the measurement standard deviation, the threshold factor and finally the threshold multiplied by B. These calculated components will be used in the following steps.

Figure 6:
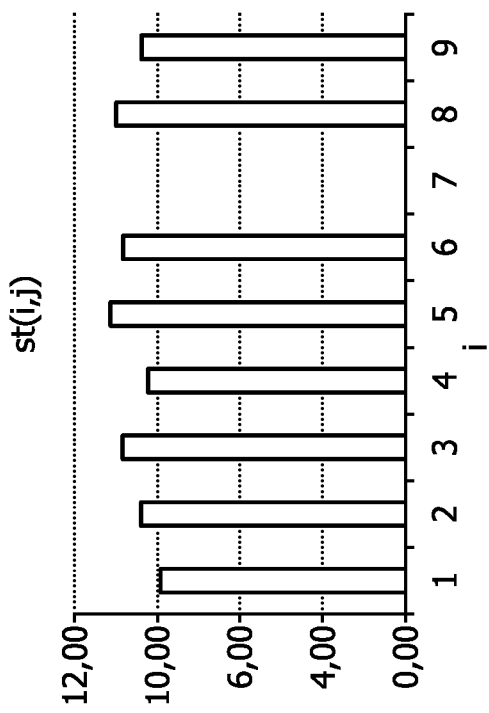
Figure 7:
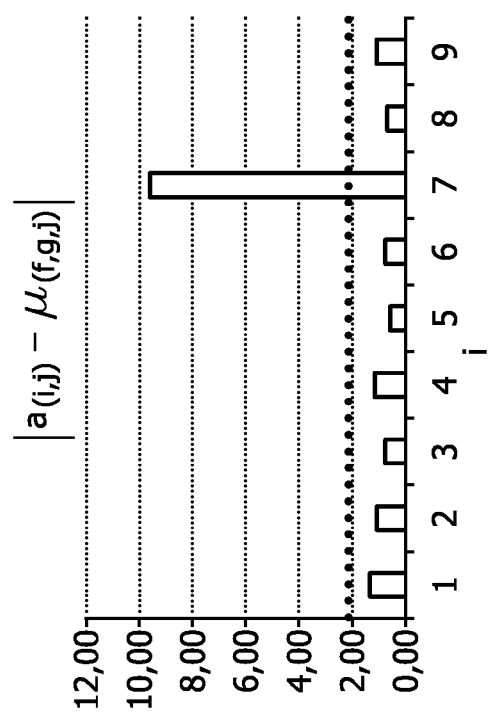

In step 3, there is calculated the absolute difference between each measurement and the measurement series average. These values are depicted in FIG. 6. There is then carried out a check as to whether the values are lower than the threshold (the threshold consists of the standard deviation times B. B can be adjusted manually). The higher the threshold, the less accurate the qualifier will be. In step 4, and in FIG. 6, it can be seen that one measurement rises above a threshold, represented by the dotted line in the Figure. In that case the stability is 0, as shown in FIG. 7. The last step calculates the average of all measurement stabilities.

The feedback information (D2 in FIG. 1) can have many different forms. For example, the measurement device 10 could be remotely reconfigured (for example locking or unlock certain additional features on the measurement device 10, changing the settings, etc.). This can be done automatically using the short feedback loop (B2 or a bit extended short loop that includes the application hosting device 14). In this case, the application hosting device 14 automatically reconfigures the measurement device 10, or the measurement device 10 does this itself. In the case of the long feedback loop, the backend server 18 does the reconfiguration. The automatic reconfiguration is guided by pre-defined rules that are triggered by the device created/calculated qualifiers 30. Examples of rules are: (stability>threshold=>perform three measurements to calculate the average), (stability<threshold=>perform five measurements to calculate the average).

Other types of feedback could be that the health care provider could stream educational material (such as an instruction video) to the subject 22 who creates the measurement. The health care provider could, once in a while, give feedback in the form of a small message which is displayed on the measurement device itself or on an accompanying application hosting device 14, providing the connectivity between the measurement device 10 and the health care provider. The health care provider could, in case of real-time data transmission, give feedback on the current measurement that is being performed.

For example, in the case of a user 22 repeating blood pressure measurements, the subject 22 uses a blood pressure meter 10 to regularly measure their blood pressure. By default, the blood pressure device 10 takes three consecutive measurements and calculates the average. The device 10 sends the measurements as data, annotated with the time of the measurements as metadata, to the system 20 of the healthcare provider via the application hosting device 14. This system 20 determines the stability qualifier for these measurements. If the stability qualifier exceeds the minimum stability threshold the system creates a feedback signal for the device 10. This signal indicates that from that moment on five measurements must be taken, making more (hopefully useable) data available to the healthcare provider systems. Next time the patient 22 attempt to measure their blood pressure, the device 10 obtains the feedback signal from the health care provider's system 20 via the application hosting device 14. On reception of the feedback signal, the device 10 reconfigures its working and will subsequently take five measurements in a row instead of three.

Blood pressure is known that to fluctuate during the day. The blood pressure meter 10 may also record the time of the measurement. This may be associated to the data 26 as metadata 28. On reception by the healthcare provider's system 20, the system 20 determines the timeliness qualifier. If this exceeds a certain threshold (for example, the patient is supposed to take the measurement at 9.00 in the morning, while he is doing that at 20.00 h) a feedback signal is created to present the patient 22 with a message, for example, "please take your measurements at 9.00 am". The blood pressure meter 10 may present this to the patient.

Figure 8:
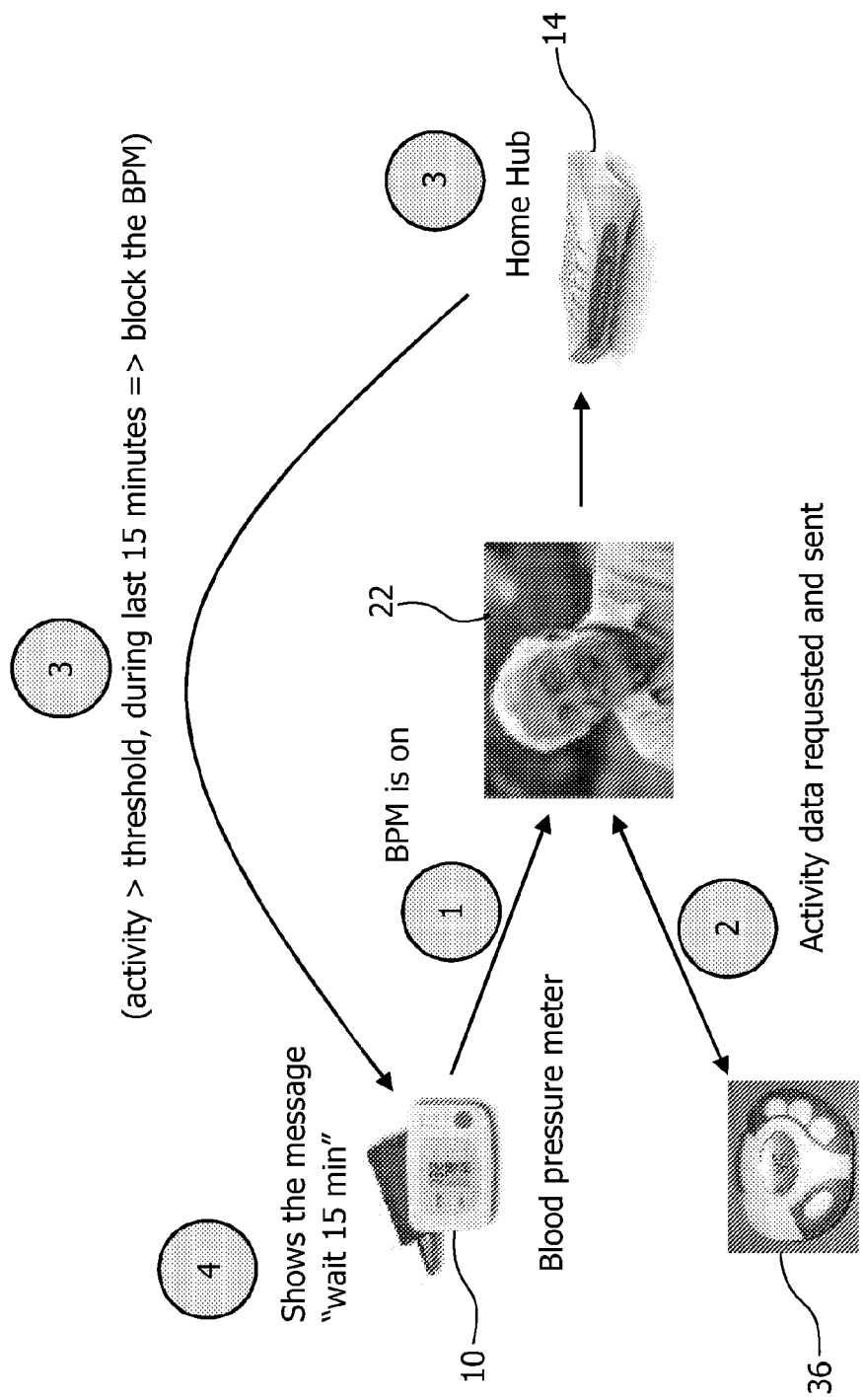
FIG. 8 is a further schematic diagram of the healthcare system.

A second example is shown in FIG. 8, which shows the interworking of a first device, the blood pressure meter 10 and, a second device, an activity monitor 36. A user may have both a blood pressure meter 10 and an activity monitor 36. For blood pressure, it is known that physical activity before the measurement affects the subject's blood pressure and the heart rate. Therefore, patients should not perform strong physical activity for a certain period of time before measuring their blood pressure.

For example, if the user 22 does perform strong physical activity, then the activity monitor 36 registers this activity. Like other measurement devices, it uploads the data to the application hosting device 14 of the Continua architecture (or to the health care provider's system—depending on the architecture). At the moment patient 22 wants to measure his blood pressure and heart rate he presses the start button of the device 10, a request for an accuracy qualifier is sent to the hosting device 14. The device 14 uses available context data, in this case physical activity data collected by the activity monitor 36, to calculate the accuracy qualifier for the blood pressure meter. This calculation can be based on rules, for example activity<threshold, during last 15 minutes=>accuracy=1, on fuzzy logics or more sophisticated classifiers.

The hosting device 14 prepares and sends the feedback signal consisting of the reconfiguration instruction to the blood pressure meter to block measurements and the feedback message "Before measuring your blood pressure refrain from strong physical activity for 15 minutes". The device 14 subsequently reconfigures its operation, to block taking measurements, and presents the message. Note that alternatively, the blood pressure measurements can be always allowed, but annotated with the level of previous physical activity to allow for correct interpretation. Then feedback can be provided with the next measurement.

It is also possible to fuse qualifiers and metadata to estimate quality. As already described, certain qualifiers and/or metadata can be used independently to estimate data quality and create the feedback information using existing techniques, such as production rules as described above. In addition, the quality estimation and feedback can be determined based on a set of qualifiers and/or metadata. This is done using existing technologies, for example, rule engines, or other classifiers that support supervised learning, such as naïve Bayes classifier, Bayesian networks, neural networks, etc. For example, a Bayesian network could be created that contains data quality as the root node and several qualifiers and/or metadata as leaf nodes (e.g. position of the blood pressure cuff, activity level of the subject 15 minutes before the measurement, stability of the measurements, etc.). The parameters of this network are learned using a training set and then the network could be applied to classify new data. Similar methods can be used to determine the feedback information directly from the metadata/qualifiers. Alternatively, the feedback information is determined based on the calculated quality estimation using other classification techniques (for example rules: if quality estimation<0.2=>feedback1, etc.). Note that the fusion process can be done on the level of metadata/qualifiers, as well as at the decision level.

The invention claimed is:

1. A method of performing measurement of a subject comprising: using a measurement device to measure a physiological parameter of a subject, wherein the measurement device further creates metadata,
   deriving, by the processor, data from the measured parameter,
   receiving, by the processor, the metadata from the measurement device, the metadata comprising information about conditions in which the measurement of the physiological parameter is taken,
   calculating, by the processor, one or more qualifiers from the derived data and from the metadata, wherein the one or more qualifiers comprise a stability qualifier that represents the stability of a series of measurements over time, wherein the stability qualifier is calculated using a stability formula,
   determining, by the processor, a quality of the derived data from the one or more qualifiers, and
   if the determined quality matches a predefined criteria, performing a predefined corrective action; wherein the corrective action is displayed to the subject via a display.

2. The method according to claim 1, wherein the step of performing a predefined corrective action comprises providing feedback to the subject.

3. The method according to claim 1, wherein the step of performing a predefined corrective action comprises performing a further measurement of the physiological parameter of the subject.

4. The method according to claim 1, wherein the step of performing a predefined corrective action comprises storing a component at a first device measuring the physiological parameter of the subject, the component adapting the future measurement of the physiological parameter of the subject.

5. The method according to claim 1, wherein the metadata comprises information about any one of: the current time, the subject's recent activity, or the number of previous measurements of the physiological parameter of the subject.

6. The method according to claim 1, wherein the stability formula calculates the stability of a single measurement using the standard deviation of the series of measurements.

7. The method according to claim 6, wherein the stability formula calculates a difference between the single measurement and the series of measurements, wherein the difference is divided by the product of a beta value times the standard deviation of the series of measurements, wherein the product of the beta value times the standard deviation defines a threshold, wherein the stability equals zero when the difference exceeds the threshold.

8. The method according to claim 7, further comprising: manually adjusting the beta value.

9. A system for performing measurement of a subject comprising: a sensor arranged to measure a physiological parameter of a subject, and to derive data from the measured parameter,
   a measurement device arranged to create metadata, the metadata comprising information about the conditions in which the measurement of the physiological parameter is taken, and
   a processor arranged to receive the derived data from the sensor and metadata from the measurement device and calculate one or more qualifiers from the derived data and/or from the metadata, wherein the one or more qualifiers comprise a stability qualifier that represents the stability of a series of measurements over time, wherein the stability qualifier is calculated using a stability formula, and determine a quality of the one or more qualifiers, and, if the determined quality matches a predefined criteria, to perform a predefined corrective action.

10. The system according to claim 9, wherein the sensor arranged to measure a physiological parameter of the subject is present in a first device, and the metadata relating to the measurement of the physiological parameter is obtained by a second device.

11. The system according to claim 9 wherein the processor is arranged, when performing a predefined corrective action, to provide feedback to the subject.

12. The system according to claim 9, wherein the processor is arranged, when performing a predefined corrective action, to request performance of a further measurement of the physiological parameter of the subject.

13. The system according to claim 9, wherein the processor is arranged, when performing a predefined corrective action, to create a component for the first device measuring the physiological parameter of the subject, the component adapting the future measurement of the physiological parameter of the subject.

14. The system according to claim 9, wherein the metadata comprises information about any one of: the current time, the subject's recent activity, or the number of previous measurements of the physiological parameters of the subject.

* * * * *